(12) United States Patent
Bergeron, Jr.

(10) Patent No.: US 6,297,287 B1
(45) Date of Patent: Oct. 2, 2001

(54) ANTI-ARRHYTHMIC COMPOSITION AND METHODS OF TREATMENT

(75) Inventor: Raymond J. Bergeron, Jr., Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

(21) Appl. No.: 09/588,706

(22) Filed: Jun. 7, 2000

Related U.S. Application Data

(63) Continuation of application No. 08/808,941, filed on Jun. 4, 1997, now Pat. No. 6,083,991.

(51) Int. Cl.$^7$ ................................................ A61K 31/135
(52) U.S. Cl. ............................................ 514/648; 514/646
(58) Field of Search ..................................... 514/646, 648

(56) References Cited

U.S. PATENT DOCUMENTS

| | | |
|---|---|---|
| 4,544,654 | 10/1985 | Davey et al. . |
| 4,629,739 | 12/1986 | Davey et al. . |
| 4,788,196 | 11/1988 | Cross et al. . |
| 4,797,401 | 1/1989 | Kemp et al. . |
| 4,806,536 | 2/1989 | Cross et al. . |
| 4,806,555 | 2/1989 | Lunsford et al. . |
| 5,091,576 * | 2/1992 | Bergeron ............................. 564/367 |
| 5,128,353 | 7/1992 | Bergeron, Jr. . |
| 5,173,505 | 12/1992 | Bergeron, Jr. . |
| 5,292,775 | 3/1994 | Bergeron, Jr. . |
| 5,342,945 | 8/1994 | Bergeron, Jr. . |
| 5,391,563 | 2/1995 | Bergeron, Jr. . |
| 5,393,757 | 2/1995 | Bergeron, Jr., et al. . |
| 5,455,277 | 10/1995 | Bergeron, Jr. . |
| 5,510,390 | 4/1996 | Bergeron, Jr. . |
| 6,083,991 | 7/2000 | Bergeron, Jr. . |

FOREIGN PATENT DOCUMENTS

| | | |
|---|---|---|
| 36 33 977 | 8/1992 | (DE) . |
| 235752 | 5/1986 | (GB) . |
| 300908 | 5/1987 | (GB) . |
| 88 300 962 | 6/1988 | (GB) . |
| 307121 | 7/1988 | (GB) . |
| 88 302 597 | 7/1988 | (GB) . |
| 88 302 598 | 7/1988 | (GB) . |
| 88 302 599 | 7/1988 | (GB) . |
| 397121 | 2/1989 | (GB) . |

OTHER PUBLICATIONS

Marmo, E. et al., "Cardiovascular and respiratory effects of spermidine and spermine: An experimental study.", Abstract to Biomed. Biochem. Acta, 43/4, pp. 509–515, 1984.*

Kecskemeti, V. et al., "Modification of the cardiac transmembrane potentials and currents by polyamines", Abstract to Eur. J. Pharmacol., 142(2), pp. 297–303, 1987.*

Goodman et al., eds., The Pharmacological Basis of Therapeutics, Sixth Edition, New York, MacMillan Publishing Co., pp. 761–767 (1980).

Edvardsson, Current Therapeutic Research, vol. 28, No. 1 Supplement, pp. 113S–118S (Jul. 1980).

Keefe et al., Drugs, vol. 22, pp. 363–400 (1981).

Classification of Anti–Arrhythmic Drugs in Symposium of Cardiac Arrhythmias, pp. 449–472, Sandoe et al., (eds.) A.B. Astra, Soederllaje, Sweden (1970).

Remington's Pharmaceutical Sciences, $4^{th}$ ed. (1970).

Guide for the Care and Use of Laboratory Animals, U.S. National Institutes of Health (NIH Publication No. 85–23, revised 1985).

Lawson, J. Pharmacol. Exper. Therap., vol. 160, pp.22–31(1968).

Marmo et al., "Cardiovascular and respiratory effects of spermidine and spermine", Biomed. Biochim. Acta 43(4), pp. 509–515, 1984.

Kecskemeti et al., "Modification of the cardiac transmembrane potentials and currents by polyamines", Eur. j. Pharmacol. 142(2), pp. 297–303, 1987.

P. Bailly et al., "Extracellular $K^{30}$Dependence of Inward Rectification Kinetics in Human Left Ventricular Cardiomyocytes"Circulation 98:2753–2759 (1998).

Bergeron et al., "Polymine Analogue Antiarrhythmics". Pharmacological Research, vol. 38, No. 5, 1998, pp. 367–380.

Tagliavini et al., "Putrescine has Anti–arhythmic Effects in Rat Models of Arrhythmia", Pharmacological Research, vol. 22, Supplement 1, 1990, pp. 125–126.

Fan and Koenig, "The Role of Polyamines in 62–Adrenergic Stimulation of Calcium Influx and Membrane Transport in Rat Heart", J. Mol. Cell. Cardiol. 20, 789–799 (1988).

Ventura et al., "Polyamine effects on $[Ca^2]_i$ homeostasis and contractility in isolated rat ventricular cardiomyocytes", Am. J. Physiol. 267:H587–592 (1994).

Busselen, "Polyamines and the Calcium Paradox in Rat Hearts", J. Mol. Cell. Cardiol. 23:237–247 (1991).

* cited by examiner

Primary Examiner—Dwayne C. Jones
(74) Attorney, Agent, or Firm—Miles & Stockbridge; Dennis P. Clarke

(57) ABSTRACT

Pharmaceutical compositions for the treatment of cardiac arrhythmia comprising an effective anti-arrhythmic amount of at least one compound in association with a pharmaceutically acceptable, substantially non-toxic carrier or excipient, the compound having one of the formulae (I) or (II) or a salt thereof with a pharmaceutically acceptable acid, and methods for the treatment of cardiac arrhythmia or effecting anti-arrhythmia action which comprise administering to a patient requiring anti-arrhythmic therapy or effect at least one of the above-described compounds.

5 Claims, No Drawings

ANTI-ARRHYTHMIC COMPOSITION AND METHODS OF TREATMENT

CROSS-REFERENCE TO RELATED APPLICATIONS

This application is a continuation of Ser. No. 08/808,941 filed on Jun. 4, 1997 now U.S. Pat. No. 6,083,991.

This application contains subject matter related to that contained in the following patent applications, the entire contents and disclosures of all of which are incorporated herein by reference: Ser. No. 06/746,672 filed Jun. 20, 1985 (abandoned); Ser. No. 07/313,734 filed Feb. 22, 1989 (U.S. Pat. No. 5,128,353); Ser. No. 07/645,644 filed Jan. 25, 1991 (U.S. Pat. No. 5,173,505); Ser. No. 07/993,620 filed Dec. 21, 1992 (U.S. Pat. No. 5,292,775); Ser. No. 06/936,835 filed Dec. 2, 1986 (abandoned); Ser. No. 06/066,227 filed Jun. 25, 1987 (abandoned); Ser. No. 07/210,520 filed Jun. 23, 1988 (U.S. Pat. No. 5,091,576); Ser. No. 07/834,345 filed Feb. 12, 1992 (U.S. Pat. No. 5,342,945); Ser. No. 07/870,441 filed Oct. 9, 1992 (abandoned); Ser. No. 07/986,576 filed Dec. 7, 1992; Ser. No. 08/061,707 filed May 17, 1993 (U.S. Pat. No. 5,393,757); Ser. No. 08/124,557 filed Sep. 22, 1993 (U.S. Pat. No. 5,391,563); Ser. No. 08/162,776 filed Dec. 8, 1993 (U.S. Pat. No. 5,455,277); and Ser. No. 08/186,985 filed Jan. 28, 1994 (U.S. Pat. No. 5,510,390).

BACKGROUND OF THE INVENTION

1. Field of the Invention

The present invention relates to novel anti-arrhythmic compositions and methods of treating cardiac arrhythmia wherein the active anti-arrhythmic agent is one of several classes of polyamines and certain derivatives thereof.

2. Description of the Prior Art

Cardiac arrhythmias are disorders involving the electrical impulse generating system of the heart. The disorders include premature contractions (extrasystoles) originating in abnormal foci in atria or ventricles, paroxysmal supraventricular tachycardia, atrial flutter, atrial fibrillation, ventricular fibrillation and ventricular tachycardia [Goodman et al, eds., *The Pharmacological Basis of Therapeutics*, Sixth Edition, New York, MacMillan Publishing Co., pages 761–767 (1980)]. More particularly, cardiac arrhythmia is a disorder of rate, rhythm or conduction of electrical impulses within the heart. It is often associated with coronary artery diseases, e.g., myocardial infarction and atherosclerotic heart disease. Arrhythmia can eventually cause a decrease of mechanical efficiency of the heart, reducing cardiac output. As a result, arrhythmia can have life-threatening effects that require immediate intervention.

Anti-arrhythmic drugs are commonly divided into four classes according to their electro-physiological mode of action. See Edvardsson, *Current Therapeutic Research*, Vol. 28, No. 1 Supplement, pages 113S–118S (July 1980); and Keefe et al, *Drugs*, Vol. 22, pages 363–400 (1981) for background information of classification first proposed by Vaughn-Williams [Classification of Anti-Arrhythmic Drugs in Symposium of Cardiac Arrhythmias, pages 449–472, Sandoe et al, (eds.) A. B. Astra, Soederlalje, Sweden (1970)].

The classification of anti-arrhythmic drugs is as follows:

I. Local anesthetic effect
II. Beta-receptor blockade
III. Prolongation of action potential duration
IV. Calcium antagonism.

Class I agents usually have little or no effect on action potential duration and exert local anesthetic activity directly at cardiac cell membrane. Class II agents show little or no effect on the action potential and exert their effects through competitive inhibition of beta-adrenergic receptor sites, thereby reducing sympathetic excitation of the heart. Class III agents are characterized by their ability to lengthen the action potential duration, thereby preventing or ameliorating arrhythmias. Class IV agents are those which have an anti-arrhythmic effect due to their actions as calcium antagonists.

Class I

Sodium Channel Depressors

These agents are efficacious in repressing a sodium current. However, these agents have no or only minute effects on the retention time of the normal action potential and decrease the maximum rising velocity ($V_{max}$) of the sodium current. They exert anti-arrhythmic activity but at the same time strongly repress cardiac functions. Careful consideration is required in administering to patients with cardiac failure or hypotension.

Class II

Beta-Blocking Agents

The agents in this class, represented by propranol-ol, are efficacious in the beta-blocking action and are useful in treating patients with arrhythmia in which the sympathetic nerve is involved. However, care must be taken in their use since these agents have side effects caused by the beta-blocking action, such as depression of cardiac functions, induction of bronchial asthmatic attack and hypoglycemic seizures.

Class III

Pharmaceutical Agents for Prolonging the Retention Time of the Action Current

These agents are efficacious in remarkably prolonging the retention time of the action current of the cardiac muscle and in prolonging an effective refractory period. Re-entry arrhythmia is considered to be suppressed by the action of the pharmaceutical agents of Class III. The medica-ments of this Class III include amiodarone and bretylium. However, all the agents have severe side effects; therefore, careful consideration is required for use.

Class IV

Calcium Antagonists

These agents control a calcium channel and suppress arrhythmia due to automatic sthenia of sinoatrial nodes and to ventricular tachycardia in which atrial nodes are contained in the re-entry cycle.

Although various anti-arrhythmic agents within the above classes are now available on the market, those having both satisfactory effects and high safety have not been obtained. For example, anti-arrhythmic agents of Class I which cause a selective inhibition of the maximum velocity of the upstroke of the action potential ($V_{max}$) are inadequate for preventing ventricular fibrillation. In addition, they have problems regarding safety, namely, they cause a depression of the myocardial contractility and have a tendency to induce arrhythmias due to an inhibition of the impulse conduction. Beta-adrenoceptor blockers and calcium antagonists which belong to Classes II and IV, respectively, have the defect that their effects are either limited to a certain type of arrhythmia or are contraindicated because of their cardiac depressant properties in certain patients with cardiovascular disease. Their safety, however, is higher than that of the anti-arrhythmic agents of Class I.

Anti-arrhythmic agents of Class III are drugs which cause a selective prolongation of the duration of the action potential without a significant depression of the $V_{max}$. Drugs in this class are limited. Examples such as sotalol and amiodarone have been shown to possess Class III properties. Sotalol also possesses Class II effects which may cause cardiac depression and are contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I anti-arrhythmic agents.

A number of anti-arrhythmic agents have been reported in the literature, such as those disclosed in EP 397,121; EP 300,908; EP 307,121; U.S. Pat. Nos. 4,629,739; 4,544,654; 4,788,196; EP application 88 302 597.5; EP application 88 302 598.3; EP application 88 302 270.9; EP application 88 302 600.7; EP application 88 302 599.1; EP application 88 300 962.3; EP application 235,752; DE 36 33 977; U.S. Pat. Nos. 4,804,662; 4,797,401; 4,806,555; and 4,806,536.

It is an object of the present invention to provide novel anti-arrhythmic pharmaceutical compositions and methods of treating cardiac arrhythmia wherein the effective anti-arrhythmic agent functions according to a mechanism substantively different from that of any of the above-described four classes of anti-arrhythmic agents. The compositions and methods of treatment of the present invention are not, therefore, subject to the above-noted disadvantages associated with the known four classes of anti-arrhythmic agents.

SUMMARY OF THE INVENTION

The present invention provides novel pharmaceutical compositions in unit dosage form for the treatment of cardiac arrhythmia comprising an effective anti-arrhythmic amount of at least one compound in association with a pharmaceutically acceptable, substantially non-toxic carrier or excipient; the compound having one of the formulae:

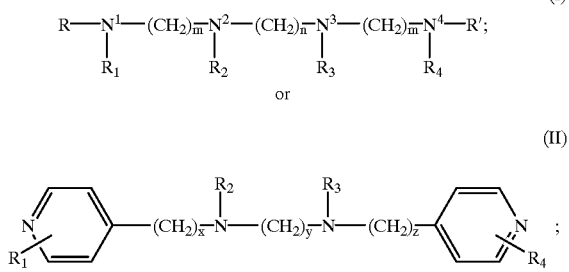

wherein:
R and R' may be the same or different and are H, alkyl, fluoroalkyl or aralkyl having from 1 to 12 carbon atoms;
$R_1$–$R_4$ may be the same or different and are H, R or R';
m and n may be the same or different and are integers from 2 to 10, inclusive; and
x, y and z may be the same or different and are integers from 0 to 8, inclusive;
or (III) a salt of (I) or (II) with a pharmaceutically acceptable acid.

The invention also provides a novel method for the treatment of cardiac arrhythmia and related heart problems or effecting anti-arrhythmic action which comprises administering to a patient requiring anti-arrhythmic therapy an anti-arrhythmic effective amount of at least one of the above-described compounds.

DETAILED DESCRIPTION OF THE INVENTION

The present invention is predicated on the discovery that the above-described polyamines (or suitable salts thereof) exert an anti-arrhythmic effect when administered to a patient in need of an anti-arrhythmic effect.

Suitable polyanines for use in the composition and methods of the present invention having the formulae (I) and (II) above, as well as derivatives and salts thereof (III) are those described in U.S. Pat. No. 5,091,576, the entire contents and disclosures of which are incorporated herein by reference. Methods for the preparation of the polyamines are also disclosed therein.

In compounds of formulae (I) and (II), R and R' are preferably methyl, ethyl, propyl, benzyl, $CF_3CH_2$—, etc., it being understood that the term "aralkyl" is intended to embrace any aromatic group the chemical and physical properties of which do not adversely affect the efficacy and safety of the compound for therapeutic applications. Preferred, however, are the hydrocarbyl aralkyl groups, i.e., comprised only of C and H atoms.

$R_1$–$R_4$ preferably are H, methyl ethyl, propyl or benzyl.

Preferred polyamines of formula (I) are those wherein (a) m is 3 and n is 4; (b) both m and n are 4; (c) R and R' are alkyl, such as methyl, ethyl and propyl; (d) R and R' are aralkyl, such as benzyl; and (e) R and R' are fluoroalkyl, such as $CF_3CH_2$—.

It will be appreciated that while the agents described above form acid addition salts and carboxy acid salts, the biological activity thereof will reside in the agent itself. These salts may be used in human medicine and presented as pharmaceutical formulations in the manner and in the amounts (calculated as the base) described herein, and it is then preferable that the acid moiety be pharmacologically and pharmaceutically acceptable to the recipient. Examples of such suitable acids include (a) mineral acids, i.e., hydrochloric, hydrobromic, phosphoric, metaphosphoric and sulfuric acids; (b) organic acids, i.e., tartaric, acetic, citric, malic, maleic, lactic, fumaric, benzoic, glycolic, gluconic, gulonic, succinic and aryl-sulfonic acids, e.g., p-toluene-sulfonic acid.

The compounds of the present invention are effective in treating and preventing all types of arrhythmias including ventricular and atrial (supraventricular) arrhythmias and associated fibrillations.

In the novel method of this invention of treating arrhythmia, a novel compound or pharmaceutically acceptable salt thereof is administered in an amount ranging from about 0.1 to about 300 mg/kg of body weight, preferably from about 0.1 to about 50 mg/kg of body weight, in a single dose, in divided doses or by intravenous infusion.

The polyamines of this invention can be administered as the sole active ingredient or in combination with other anti-arrhythmic agents or other cardiovascular agents.

The polyamines or pharmaceutically acceptable salts thereof of the present invention in the described dosages are administered orally, intraperitoneally, subcutaneously, intramuscularly, transdermally, sublingually or intravenously. They are preferably administered orally, for example, in the form of tablets, troches, capsules, elixirs, suspensions, syrups, wafers, chewing gum or the like prepared by art recognized procedures. The amount of active compound in such therapeutically useful compositions or preparations is such that a suitable dosage will be obtained.

The pharmaceutical compositions of the invention preferably contain a pharmaceutically acceptable carrier or excipient suitable for rendering the compound or mixture administrable orally as a tablet, capsule or pill, or parenterally, intravenously, intradermally, intramuscularly or subcutaneously, rectally, via inhalation or via buccal administration, or transdermally. The active ingredients may be admixed or compounded with any conventional, pharmaceutically acceptable carrier or excipient. It will be understood by those skilled in the art that any mode of administration, vehicle or carrier conventionally employed and which is inert with respect to the active agent may be utilized for preparing and administering the pharmaceutical compositions of the present invention. Illustrative of such methods, vehicles and carriers are those described, for example, in *Remington's Pharmaceutical Sciences,* 4th ed. (1970), the disclosure of which is incorporated herein by reference. Those skilled in the art, having been exposed to the principles of the invention, will experience no difficulty in determining suitable and appropriate vehicles, excipients and carriers or in compounding the active ingredients therewith to form the pharmaceutical compositions of the invention.

The therapeutically effective amount of active agent to be included in the pharmaceutical composition of the invention depends, in each case, upon several factors, e.g., the type, size and condition of the patient to be treated, the intended mode of administration, the capacity of the patient to incorporate the intended dosage form, etc.

While it is possible for the agents to be administered as the raw substances, it is preferable, in view of their potency, to present them as a pharmaceutical formulation. The formulations of the present invention for human use comprise the agent, together with one or more acceptable carriers therefor and optionally other therapeutic ingredients. The carrier(s) must be "acceptable" in the sense of being compatible with the other ingredients of the formulation and not deleterious to the recipient thereof. Desirably, the formulations should not include oxidizing agents and other substances with which the agents are known to be incompatible. The formulations may conveniently be presented in unit dosage form and may be prepared by any of the methods well known in the art of pharmacy. All methods include the step of bringing into association the agent with the carrier which constitutes one or more accessory ingredients. In general, the formulations are prepared by uniformly and intimately bringing into association the agent with the carrier(s) and then, if necessary, dividing the product into unit dosages thereof.

Formulations suitable for parenteral administration conveniently comprise sterile aqueous preparations of the agents which are preferably isotonic with the blood of the recipient. Suitable such carrier solutions include phosphate buffered saline, saline, water, lactated ringers or dextrose (5% in water). Such formulations may be conveniently prepared by admixing the agent with water to produce a solution or suspension which is filled into a sterile container and sealed against bacterial contamination. Preferably, sterile materials are used under aseptic manufacturing conditions to avoid the need for terminal sterilization.

Such formulations may optionally contain one or more additional ingredients among which may be mentioned preservatives, such as methyl hydroxybenzoate, chlorocresol, meta-cresol, phenol and benzalkonium chloride. such materials are of special value when the formulations are presented in multi-dose containers.

Buffers may also be included to-provide a suitable pH value for the formulation. Suitable such materials include sodium phosphate and acetate. Sodium chloride or glycerin may be used to render a formulation isotonic with the blood. If desired, the formulation may be filled into the containers under an inert atmosphere such as nitrogen or may contain an anti-oxidant, and are conveniently presented in unit dose or multi-dose form, for example, in a sealed ampoule.

Those skilled in the art will be aware that the amounts of the various components of the compositions of the invention to be administered in accordance with the method of the invention to a patient will depend upon those factors noted above.

The compositions of the invention when given orally or via buccal administration may be formulated as syrups, tablets, capsules and lozenges. A syrup formulation will generally consist of a suspension or solution of the compound or salt in a liquid carrier, for example, ethanol, glycerine or water, with a flavoring or coloring agent. Where the composition is in the form of a tablet, any pharmaceutical carrier routinely used for preparing solid formulations may be employed. Examples of such carriers include magnesium stearate, starch, lactose and sucrose. Where the composition is in the form of a capsule, any routine encapsulation is suitable, for example, using the aforementioned carriers in a hard gelatin capsule shell. Where the composition is in the form of a soft gelatin shell capsule, any pharmaceutical carrier routinely use for preparing dispersions or suspensions may be considered, for example, aqueous gums, celluloses, silicates or oils, and are incorporated in a soft gelatin capsule shell.

A typical suppository formulation comprises the polyamine or a pharmaceutically acceptable salt thereof which is active when administered in this way, with a binding and/or lubricating agent, for example, polymeric glycols, gelatins, cocoa-butter or other low melting vegetable waxes or fats.

Typical transdermal formulations comprise a conventional aqueous or non-aqueous vehicle, for example, a cream, ointment, lotion or paste or are in the form of a medicated plastic, patch or membrane.

Typical compositions for inhalation are in the form of a solution, suspension or emulsion that may be administered in the form of an aerosol using a conventional propellant such as dichlorodifluoromethane or trichlorofluoromethane.

The compositions of the present invention may be co-administered with other pharmaceutically active compounds, for example, in combination concurrently or sequentially. Conveniently, the compound of this invention and the other active compound or compounds are formulated in a pharmaceutical composition. Examples of compounds which may be included in pharmaceutical compositions with the polyamines of the invention include vasodilators, for example, hydralazine; angio-tensin converting enzyme inhibitors, for example, captopril; anti-anginal agents, for example, isosorbide nitrate, glyceryl trinitrate and pentaerythritol tetranitrate; anti-arrhythmic agents, for example, quinidine, procainamide and lignocaine; cardioglycosides, for example, digoxin and digitoxin; calcium antagonists, for example, verapamil and nifedipine; diuretics, such as thiazides and related compounds, for example, bendrofluazide, chlorothiazide, chlorothalidone, hydrochlorothiazide and other diuretics, for example, fursemide and triamterene, and sedatives, for example, nitrazepam, flurazepam and diazepam.

The invention is illustrated by the following non-limiting examples.

EXAMPLE 1

Isoproterenol is known to induce arrhythmias in mammals when administered thereto in large doses. The following tests were carried out to ascertain the efficacy of the above-described polyamines in preventing isoproterenol-induced arrhythmias and deaths.

Desoxycorticosterone acetate, d,l-propranolol and isoproterenol were obtained commercially. The polyamine analogues were synthesized as described in U.S. Pat. No. 5,091,576 and put into solution with sterile normal saline. The drug solutions were made fresh for each experiment.

Male Wistar rats (275–300 g) were obtained from Charles River laboratories (Wilmington, Mass.). The animals were housed in a temperature- and humidity-controlled room. This investigation conforms with the *Guide for the Care and Use of Laboratory Animals* published by the U.S. National Institutes of Health (NIH Publication No. 85-23, revised 1985).

Briefly, rats were anesthetized with sodium pentobarbital (55 mg/kg. i.p.), and a 25 mg pellet of desoxycorticosterone acetate (DOCA) was implanted s.c. in the axillary region. The rats were allowed to recover from the anesthetic and returned to their home cages. The animals were given commercial rat chow and a 1% solution of saline as their drinking fluid ad libitum. The animals were maintained on this regimen for approximately thirty days. After this time, the animals were weighed and randomly assigned to one of three treatment protocols: (1) the identification of anti-arrhythmic agents and a dose response of the effective compounds. (Section A hereinbelow); (2) arrhythmia prevention studies including electrocardiogram (EKG), blood pressure and heart rate determinations (Section B hereinbelow); and (3) the induction and reversal of an established arrhythmia (section C hereinbelow).

A. Testing of Polyamine Analogues for Anti-arrhythmic Properties

In order to identify compounds with anti-arrhythmic properties suitable for further study, unrestrained, conscious rats were weighed, placed in individual cages and given a s.c. injection of either a positive control (d,l-propranolol, 1 mg/kg), a negative control (saline placebo) or a polyamine analogue. Twenty minutes later, the rats were challenged with a single s.c. dose of isoproterenol, 150 mg/kg. The animals were closely monitored for one hour and any obvious arrhythmic episodes or mortalities were recorded. A dose response was performed on compounds displaying anti-arrhythmic properties.

B. Evaluation of Blood Pressure, Heart Rate and EKG

Blood pressure and heart rate parameters, as well as an EKG, were evaluated for compounds displaying anti-arrhythmic properties. The animals were implanted with DOCA and maintained on 1% saline as their drinking fluid as discussed above. The animals were anesthetized with Avertin (tribromoethanol, 2.5%), 1 ml/100 g given i.p. and prepared for the recording of blood pressure and the EKG. To allow for the direct measurement of blood pressure, the animals's left carotid artery was cannulated with PE-50 tubing. The tubing was filled with saline and exteriorized dorsally between the animal's shoulders.

After the surgery was completed, the catheter in the carotid artery was connected to a blood pressure transducer (ADInstruments, Inc., Milford, Mass.). To allow for the recording of the EKG, 22 gauge needles were placed s.c. at the rat's left shoulder, right shoulder and left leg. The needles were then attached via alligator clips to a MacLab Bio Amplifier (ADInstruments, Inc., Milford, Mass.). The blood pressure transducer and the MacLab Bio Amplifier were, in turn, connected to a MacBridge 4 (ADInstruments, Inc., Milford, Mass.), a computer-controlled transducer interface. The data were then transmitted to the MacLab 4e data acquisition system powered by a Macintosh Quadra 650. The MacLab Chart program was used to display and analyze the data. A baseline blood pressure, heart rate and EKG were obtained, and the compound under investigation was administered s.c. Twenty minutes later, the animals were challenged with a single dose of isoproterenol, 150 $\mu$g/kg s.c. Continuous blood pressure, heart rate and EKG readings were obtained. Additional Avertin was given as needed to maintain anesthesia. The hearts of the animals were perfused with buffered formalin immediately after the onset of ventricular fibrillation or one hour after the administration of the isoproterenol.

C. Arrhythmic Reversal Studies

The animals were implanted with a 25 mg pellet of DOCA and maintained on the 1% saline as their drinking fluid as discussed above. The animals were anesthetized with Avertin and prepared for the recording of blood pressure and the EKG. In addition, the animal's left jugular vein was also cannulated with PE-50 tubing. The tubings were filled with saline and exteriorized dorsally between the animal's shoulders. Isoproterenol was administered s.c. at a dose of 150 $\mu$g/kg and an arrhythmia was allowed to develop for five minutes. After this time, either propranolol or the compound of interest was given as an intravenous bolus at one-half of the effective s.c. dose. Continuous blood pressure, heart rate and EKG readings were obtained. Additional Avertin was given as needed to maintain anesthesia. The hearts of the animals were perfused with buffered formalin immediately after the onset of ventricular fibrillation or one hour after the administration of isoproterenol.

The data are presented as the mean ± s.e.m. Statistical analyses of the data were performed by use of the Student's t-test. A value of P<0.05 was considered significant.

Two kinds of anti-arrhythmic experiments were carried out, both prophylaxis and reversal studies. DOCA-treated animals were either first given the test compounds s.c. followed twenty minutes later by isoproterenol (prevention studies) or isoproterenol followed by the test compound given intravenously after five minutes (reversal studies). The time frames were chosen based on two issues: previous experience with the pharmacokinetics of polyamine analogues and the time required for isoproterenol to induce cardiac abnormalities and death in DOCA-treated rodents.

Within the boundary conditions of these studies, 95% of all DOCA/isoproterenol-treated controls were dead within one hour and abnormal cardiac electrical events usually began within five minutes which is in keeping with reports in the literature. Propranolol served as the positive control in both the prophylactic and reversal experiments. In order to compare the compounds, all dosages are recorded in both mg/kg and $\mu$mol/kg. Finally, the reversal studies only focus on the most effective prophylactic device PYR(3,3,3).

Under these experimental conditions, propranolol was clearly the more effective prophylactic and reversal device from a dosage perspective. Beyond this, the behavior of the polyamines was rather varied. Surprisingly, putrescine had no effect on survival in this system, even at concentrations higher than those reported in the earlier aconitine and reperfusion arrhythmia models.

As described above, all three of the tetraamines DENSPM, DESPM and DEHSPM are very potent polyamine anti-metabolites: all three are tetracations at physiologic pH. Interestingly, none of the three polyamine anti-metabolites tested in this model had any effects on the survival of DOCA/isoproterenol-treated rats. PIP(3,3,3), a cyclic aliphatic tetraamine, is largely a trication at physiologic pH; this compound was not an effective polyamine anti-metabolite, nor was it found to be active in this model.

The remainder of the compounds investigated were all largely dications at physiological pH. FDESPM, a molecule of very similar geometry to DESPM, did indeed show some anti-arrhythmic prophylactic behavior with 40% of the animals surviving. This dicationic tetraamine has both charges at the two central nitrogens. When the charges are moved farther apart as in DE(9), the compound has no activity.

Of the pyridine tetraamines investigated, PYR(3,3,3), PYR(3,4,3) and PYR(4,4,4) all presented with anti-arrhythmic properties. The two most active compounds, PYR(3,3,3) and PYR(3,4,3), demonstrated a clear dose response. Because of the minimal activity of the PYP(4,4,4) system, a dose-response study was not run.

In light of earlier results indicating that both DEHSPM and DENSPM lower blood pressure in normotensive rats, continuous monitoring of blood pressure and heart rate was performed on animals treated with propranolol and PYR(3,3,3). No appreciable effects on blood pressure and heart rate were observed in rats treated with PYR(3,3,3).

From a prevention perspective, PYR(3,3,3) performed best. PYR(3,3,3) was also evaluated in reversal experiments. DOCA-treated animals were given isoproterenol and allowed to enter an arrhythmic event. Isoproterenol given intravenously in these animals induces an event within one minute. The animals were then treated with saline, propranolol or PYR(3,3,3) five minutes after isoproterenol. Animals given saline quickly died of ventricular fibrillation; animals treated with propranolol not only survived, but also had EKG's that reverted to a more normal pattern. However, there was some evidence of ischemia. In contrast, the EKG's in animals given PYR(3,3,3) reverted to a normal appearance and showed little to no evidence of ischemia.

The above-discussed results are presented in the following table.

TABLE

EFFECT OF POLYAMINE ANALOGUES ON THE INCIDENCE
OF MORTALITY PRODUCED BY ISOPROTERENOL
IN DOCA/SALINE PRE-TREATED RATS

| TREATMENT | DOSE (MG/KG) | ($\mu$MOL/KG) | N= | ARRHYTHMIA | % SURVIVAL |
|---|---|---|---|---|---|
| Control | — | — | 20 | 20 | 5 |
| Propranolol | 1 | 3.4 | 5 | 0 | 100 |
| DENSPM(3, 3, 3) | 90.27 | 231 | 5 | 5 | 0 |
| DESPM(3, 4, 3) | 46.7 | 115 | 5 | 5 | 0 |
| DEHSPM(4, 4, 4) | 50 | 115 | 5 | 5 | 0 |
| PIP(3, 3, 3) | 44.6 | 115 | 5 | 5 | 0 |
| Putrescine (4) | 18.6 | 115 | 5 | 5 | 0 |
| | 200 | 1240 | 5 | 5 | 0 |
| | 300 | 1861 | 5 | 5 | 0 |
| DE(9) | 33.2 | 115 | 5 | 5 | 0 |
| FDESPM | 59.1 | 115 | 10 | 7 | 40 |
| PYR(3, 3, 3) | 4.38 | 14 | 5 | 5 | 40 |
| | 8.75 | 28 | 5 | 5 | 40 |
| | 17.5 | 59 | 5 | 4 | 60 |
| | 35 | 115 | 6 | 2 | 100 |
| PYR(3, 4, 3) | 18.2 | 59 | 5 | 2 | 60 |
| | 36.4 | 115 | 5 | 2 | 60 |
| | 72.8 | 231 | 5 | 2 | 80 |

TABLE-continued

EFFECT OF POLYAMINE ANALOGUES ON THE INCIDENCE
OF MORTALITY PRODUCED BY ISOPROTERENOL
IN DOCA/SALINE PRE-TREATED RATS

| TREATMENT | DOSE (MG/KG) | ($\mu$MOL/KG) | N= | ARRHYTHMIA | % SURVIVAL |
|---|---|---|---|---|---|
| PYR(4, 4, 4) | 48 | 115 | 5 | 5 | 0 |
| | 96 | 231 | 5 | 2 | 40 |
| PYR(5, 4, 5) | 51.6 | 115 | 5 | 5 | 0 |

DEHSPM(4,4,4)=diethylhomospermine
DENSPM(3,3,3)=diethylnorspermine
DESPM(3,4,3)=diethylspermine

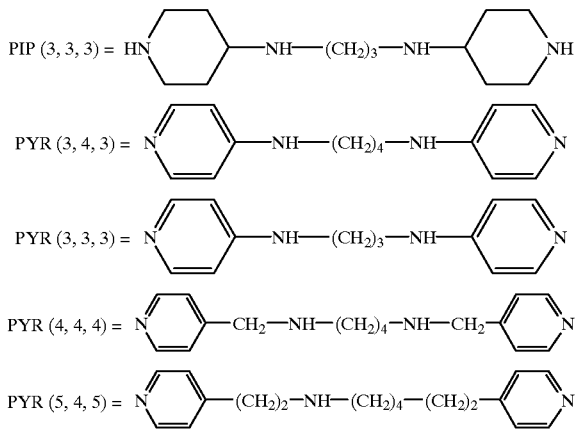

FDESPM(3,4,3)=Di-$\beta,\beta,\beta$-trifluoroethylspermine
DE(9)=$C_2H_5$—NH—$(CH_2)_9$—NH—$C_2H_5$

EXAMPLE 2

In this procedure [Lawson, *J. Pharmacol. Exper. Therap.*, Vol. 160, pages 22–31 (1968)], the test substance [diethylhomospermine (DEHSPM)] is administered i.p. (100 mg/kg) to a group of three mice thirty minutes before exposure to deep chloroform anesthesia and observed during the ensuing 15-minute period. Absence of EKG recorded cardiac arrhythmias and heart rates above 200 beats per minute present (usual =400–480 beats per minute) in none or only one (<2) of three animals indicates significant protection.

Only one animal exhibited cardiac arrhythmia, thereby demonstrating the anti-arrhythmic activity of DEHSPM.

I claim:
1. A pharmaceutical composition in unit dosage form for the treatment of cardiac arrhythmia comprising an effective anti-arrhythmic amount of at least one compound in association with a pharmaceutically acceptable, substantially non-toxic carrier or excipient; said compound having one of the formulae:

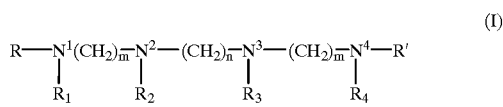

-continued or

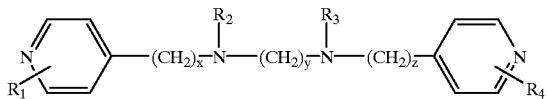
(II)

wherein:

R and R' may be the same or different and are fluoroalkyl or aralkyl having from 1 to 12 carbon atoms;

$R_1-R_4$ may be the same or different and are H, alkyl, fluoroalkyl or aralkyl having from 1 to 12 carbon atoms;

m and n may be the same or different and are integers from 2 to 10, inclusive; and x, y and z may be the same or different and are integers from 0 to 4, inclusive; or a salt of (I) or (II) with a pharmaceutically acceptable acid.

2. A composition according to claim 1 wherein m is 3 and n is 4.

3. A composition according to claim 1 wherein m and n are 4.

4. A composition according to claim 1 wherein R and R' are aralkyl.

5. A composition according to claim 1 wherein R and R' are $CF_3CH_2$—.

* * * * *